(12) United States Patent
Morelle et al.

(10) Patent No.: US 6,492,302 B1
(45) Date of Patent: Dec. 10, 2002

(54) COMPOSITIONS FOR THE PROTECTION OF PLANTS AGAINST THE STRESS OF OXIDATION

(76) Inventors: Jean Morelle, 170, Avenue Parmentier, 75010 Paris (FR); Eliane Lauzanne, 57, Avenue de la Republique, 75011 Paris (FR); Jacqueline Rothfuss, 14, Rue du Faubourg, 67630 Lauterbourg (FR); Christophe De Mil, 7, Rue Mechain, 75014 Paris (FR)

( * ) Notice: Subject to any disclaimer, the term of this patent is extended or adjusted under 35 U.S.C. 154(b) by 0 days.

(21) Appl. No.: 09/719,952
(22) PCT Filed: Jun. 14, 1999
(86) PCT No.: PCT/FR99/01400
§ 371 (c)(1),
(2), (4) Date: Jun. 20, 2001
(87) PCT Pub. No.: WO99/65304
PCT Pub. Date: Dec. 23, 1999

(30) Foreign Application Priority Data

Jun. 17, 1998 (FR) ............................................. 98 07613

(51) Int. Cl.$^7$ ................................................ A01N 37/00
(52) U.S. Cl. ...................................... 504/142; 504/307
(58) Field of Search .................................. 504/142, 307

(56) References Cited

FOREIGN PATENT DOCUMENTS

GB        2200633    *    8/1988

* cited by examiner

*Primary Examiner*—Alton Pryor
(74) *Attorney, Agent, or Firm*—Lucas & Just

(57) ABSTRACT

This invention concerns making compounds destined for the protection of plants against oxidative stress, characterized by lipo-amino acids enriched with methionine during a process of acylation with hydrolysates of proteins or of amino acids taken individually or combined; or after acylation and lipo-amino acids partially or totally salified by basic amino acids which gives them antioxidant and antifree radical properties. This invention extends to the total or partial salification of this type of lipo-amino acids with oligoelements.

10 Claims, No Drawings

COMPOSITIONS FOR THE PROTECTION OF PLANTS AGAINST THE STRESS OF OXIDATION

This application is a 371 of PCT/FR 99/01400 filed Jun. 14, 1999.

It is well-known that many plants are sensitive to drops in temperature, even above the freezing point. This is the case for most fruit-bearing trees.

It has been determined that frost and other fluctuations in temperature, including dryness and excessive heat, are aggressive to plant life, generating a phenomenon defined as "oxidative stress", defined as an accelerated and excessive generation of free radicals: alkoxy, peroxy, and oxygen singlets. These free radicals are produced by the interaction of lipooxygenase with the lipids of cell membranes.

In the case of excessive dryness, the formation of superoxidated anions ($O_2°$) among the plant chloroplasts has been observed.

This oxidative stress leads to the formation of derivatives toxic to living cells such as malondialdehyde (MDA), this last substance being an indicator of the level of oxidative deterioration. Lipoperoxidation is indicated by the reaction of thiobarbituric acid with MDA.

The accumulation of lipoperoxides provokes an activation of the senescence of the leaves and dicotyledons.

It has been determined that the senescent leaves and dicotyledons accumulated fluorescent substances are derived from the oxidative process of unsaturated fatty acids. These fluorescent substances are also the end products of peroxidation, obtained by the interaction of aldehydic functions, particularly that of MDA upon the amino function of the proteins.

This oxidative stress provokes a decrease in superoxide dismutase (SOD), as well as a perturbation of membranoid proteins, as we have observed notably in vegetables.

The degenerative activity of lipid peroxidation is evident not only for plants at various stages of growth but also during the period of seed germination, according to the levels of hydroperoxidation present.

Many plants are rich in polyphenols (flavonoids) which are powerful antioxidants. The levels of these polyphenols are more elevated in plants in sunlight than in those located in the shade.

The present invention is intended to protect plants against the aforementioned oxidative stress with the use of compounds of lipo-amino acids specifically selected for their capacity as antioxidants.

Compounds of lipo-amino acids have been previously described as active agents for the stimulation of vegetal biosynthesis, or as fertilizing agents. These structures have also been cited as having antibacterial and antifungal properties in the following patents: FR-A-2 403 024, FR-A-2 503 153, FR-A-2 503 144.

The French patent FR-A-2 503 151 also mentions sulpho-butyryl-amino acids such as methionine or cystine but not in relation to any protection against lipoperoxidation. It is only recently that the antioxidant properties of butyryl-methionine have been discovered; butyryl-cystine, on the other hand, does not possess these properties.

French patent FR-A-85 137 38 concerns the utilization of lipo-amino acids and their salts to increase floral fertility. It is also a highly specified process.

French patent FR-A-2 503 153 concerns lipo-amino acids of proline and hydroxyproline which have specific effects upon dryness in plant life.

Later studies upon lipo-amino acids of proline have shown that those compounds also protected against the adverse effects of frost.

Within the scope of the experiments performed which have led to the present discovery it has been determined that the sole utilization of lipo-amino acids of proline, which have no antioxidant properties, enhanced the survival rate by 40% among treated specimens exposed to temperatures of −7° C. for a period of three hours. Whereas a lipo-amino acid compound comprised of 70% proline and 30% methionine increased resistance to frost, with increased survival rates of 60% to 75%. There was a clear indication that the antioxidant properties of the methionine lipo-amino acids had a direct impact upon the oxidative stress levels created by frost.

Identical results were obtained upon the addition of methionine during the acylation of amino acids derived from hydrolized animal or vegetable proteins and when lipo-amino acids have their carboxyls neutralized by the basic amino acids lysine and arginine.

Experiments testing the effects of dryness performed upon cotton plants showed an increase in their resistance to dehydration.

The addition of antioxidant lipo-amino acids to lipo-amino acids of copper or zinc salts (indicated in examples) has resulted in several conclusions:

an increase of resistance to Botrytis and an increase of 10 to 20% in the photosynthesis of vines;

increased germinative activity in seeds increased yields of linseed, corn, wheat, barley and sunflower crops.

As a result of these developments, the present discovery can be described by the use of specifically selected lipo-amino acid compounds, defined by:

Fatty acid chains of 4 to 22 atoms of carbon, with a preference for the butyric (C4) and octanoyl (C8) chains. These fatty acid chains are acylated, either to individual or combined amino acids or to amino acids from hydrolysates of animal or vegetable proteins, enriched with a minimum of 5% methionine.

The lipo-amino acids thus obtained can be salified or not by oligoelements, preferably copper or zinc or by the basic amino acids lysine or arginine.

The invention extends to the addition of methionine to enrich compounds of lipo-amino acids poor in methionine, salified or not by oligoelements.

The invention extends equally to the use of lipo-amino acids, whether individual or combined, with carboxyls neutralized by the basic amino acids lysine or arginine with their established antioxidant properties, to be used alone or in conjunction with lipo-amino acids salified or not by oligo-elements.

These different substances are administered based upon the nature of the plants, from 50 to 1000 grams per hectare.

The following is a list, by no means limited, of possible uses of the previously described compounds:

1) For the treatment of seeds

Copper salts of the acid of butyryl-amino acids containing 5 to 30% of butyryl-methionine Copper salts of the acid of octanoyl-amino acids with 5 to 50% of octanoyl-amino acids with a 20% mix of octanoyl-methionine.

Double salts of zinc and lysine of the acids of butyryl-amino acids.

Octanoyl-glycinate of lysine.

Butyryl-prolinate of lysine.

2) For the treatment of vines

Copper salts of octanoyl-amino acids with 30% of octanoyl-methionine.

Copper salts of butyryl-amino acids containing 5 to 20% of methionine.

Double salts of copper and lysine butyryl-amino acids.
Octanoyl-methionate of lysine.

3) For the treatment of potatoes

Copper salts of octanoyl-amino acids, 30% of which are composed of octanoyl-methionine.

Copper salts of butyryl-amino acids, 5 to 20% of which are methionine.

Double salts of copper and lysine butyryl-amino acids.
Octanoyl-methionate of lysine.

4) For the treatment of wheat crops

Copper salts of butyryl-amino acids containing 20% methionine.

A mixture of copper salts of octanoyl-amino acids with 30% of acids of lysine-octanoyl-amino acids.

Mixture ratios:

| | |
|---|---|
| Octanoyl-glycinate of lysine | 50% |
| Butyryl-methionate of lysine | 50% |

What is claimed is:

1. A process for protection of plants against oxidative stress comprising administration of lipo-amino fatty acid compounds containing fatty acid chains having from 4 to 22 atoms of carbon to said plants, wherein said fatty acid chains are acylated to amino acids derived from hydrolysates of proteins of animal or vegetable origin and enriched in methionine.

2. The process of claim 1, wherein the acid chains are butyryl (C4) fatty acid chains or octanoyl (C8) fatty acid chains.

3. The process of claim 1, wherein said fatty acid chains are enriched with a minimum of 5% methionine.

4. The process of claim 1, comprising the addition of a lipo-amino acid of methionine.

5. The process of claim 1, further comprising individual or combined lipo-amino acids enriched with methionine.

6. The process of claim 5, wherein the methionine is salified with lysine or arginine.

7. The process of claim 1, comprising fatty acid chains with carboxyls neutralized by the basic amino acids lysine or arginine.

8. The process of claim 7 wherein the fatty acid chains are salified by oligoelements.

9. The process of claim 1 wherein the lipo-amino fatty acid compounds are administered to the plants at the rate of 50 to 1000 grams per hectare.

10. A process for protection of plants against oxidative stress comprising administration of lipo-amino fatty acid compounds containing fatty acid chains having from 4 to 22 atoms of carbon, said fatty acid chains being salified by at least one oligoelement selected from the group comprising copper and zinc, wherein said fatty acid chains are acylated to amino acids derived from hydrolysates of proteins of animal or vegetable origin and enriched in methionine.

* * * * *